United States Patent
Huber et al.

(10) Patent No.: US 9,283,408 B2
(45) Date of Patent: Mar. 15, 2016

(54) RIGID APPARATUS TO REPLACE BEAM STEERING

(71) Applicant: ProNova Solutions, LLC, Knoxville, TN (US)

(72) Inventors: Jonathan Huber, Knoxville, TN (US); Alan Henley, Knoxville, TN (US)

(73) Assignee: ProNova Solutions, LLC, Knoxville, TN (US)

( * ) Notice: Subject to any disclaimer, the term of this patent is extended or adjusted under 35 U.S.C. 154(b) by 0 days.

(21) Appl. No.: 14/492,968

(22) Filed: Sep. 22, 2014

(65) Prior Publication Data

US 2015/0087884 A1   Mar. 26, 2015

Related U.S. Application Data

(60) Provisional application No. 61/880,327, filed on Sep. 20, 2013.

(51) Int. Cl.
    *G21K 5/04* (2006.01)
    *A61N 5/10* (2006.01)

(52) U.S. Cl.
    CPC ............ *A61N 5/1082* (2013.01); *A61N 5/1081* (2013.01); *A61N 2005/1087* (2013.01)

(58) Field of Classification Search
    USPC ........... 250/396 R, 397, 398, 396 ML, 492.1, 250/492.2, 492.3; 600/1
    See application file for complete search history.

(56) References Cited

U.S. PATENT DOCUMENTS

| | | | |
|---|---|---|---|
| 5,097,132 A | 3/1992 | Plummer | |
| 7,372,053 B2 | 5/2008 | Yamashita et al. | |
| 7,381,979 B2 | 6/2008 | Yamashita et al. | |
| 7,961,844 B2 | 6/2011 | Takeda et al. | |
| 2004/0159795 A1 | 8/2004 | Kaercher et al. | |
| 2007/0284548 A1 | 12/2007 | Kaiser et al. | |
| 2008/0234531 A1* | 9/2008 | Welch ...................... A61N 5/10 600/2 |
| 2011/0156703 A1 | 6/2011 | O'Connor | |
| 2012/0224667 A1 | 9/2012 | Cheng et al. | |
| 2012/0313003 A1 | 12/2012 | Trbojevic | |
| 2013/0032731 A1 | 2/2013 | Tombrello, Jr. et al. | |

(Continued)

FOREIGN PATENT DOCUMENTS

WO    WO2011036254    3/2011

OTHER PUBLICATIONS

Norimine et al., "A Design of a Rotating Gantry with Easy Steering for Proton Therapy", Proceedings of EPAC, 2002, pp. 2751-2753 [online], URL=<http://accelconf.web.cern.ch/Accelconf/e02/PAPERS/MOPRI094.pdf.>.

(Continued)

*Primary Examiner* — Nicole Ippolito
(74) *Attorney, Agent, or Firm* — Pitts & Lake. P.C.

(57) ABSTRACT

A proton beam delivery system including a proton beam nozzle to emit a proton beam to a targeted region of a patient, a gantry wheel to support the proton beam nozzle, the gantry wheel being configured to rotate the proton beam nozzle about a rotation axis of the gantry wheel such that the proton beam nozzle emits the proton beam to an isocenter of the gantry wheel corresponding to the targeted region, a beamline deflector configured to be rotated by the gantry wheel to transport the proton beam along a curvilinear path from the rotation axis to the proton beam nozzle using a predetermined power setting of the beamline deflector, and a rigid support structure to support the beamline deflector when the gantry wheel is rotated such that the beam nozzle directs the proton beam to the isocenter from a plurality of radial directions using the same predetermined power setting.

20 Claims, 7 Drawing Sheets

(56) References Cited

U.S. PATENT DOCUMENTS

2014/0121442 A1    5/2014   Matteo et al.
2014/0275699 A1*   9/2014   Benna et al. .................. 600/1

OTHER PUBLICATIONS

Vorobiev et el.,"Concepts of a compact achromatic proton gantry with a wide scanning field"; Nuclear Instruments and Methods in Physics Research, 1998, entire document [online] URL=>http://ac.els-cdn.com/S0168900298919908/1-s2.0-S0168900298919908-main.pdf?_tid    +5ce42094-9ccd-11e4-98d9-00000aab0f02&acdnat=1421336836_507b7a3bfa5dcb57a1aa1a7750954f1>.

Patent Cooperation Treaty; Int'l Search Report & Written Opinion, Form PCT/ISA/220 (Jul. 2014 Feb. 9, 2015), Date of Mailing: Apr. 1, 2015.

* cited by examiner

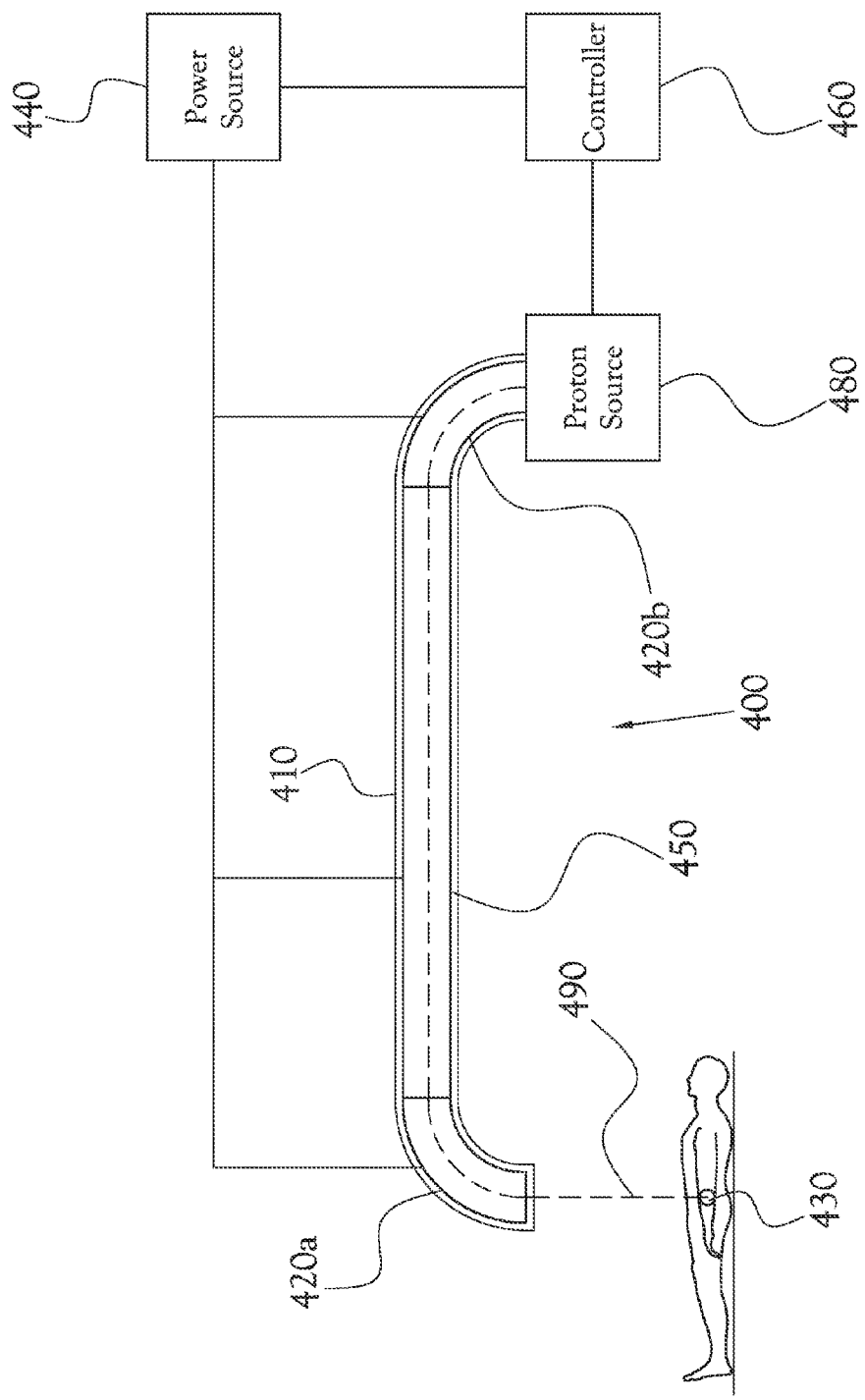

RIGID APPARATUS TO REPLACE BEAM STEERING

CROSS-REFERENCE TO RELATED APPLICATIONS

This application claims the benefit of U.S. Provisional Patent Application Ser. No. 61/880,327, filed on Sep. 20, 2013, the disclosure of which is incorporated herein in its entirety by reference.

FIELD OF INVENTION

The present general inventive concept relates to proton therapy for cancer treatment, and, more particularly, to a rotating gantry system with a superconducting beamline.

BACKGROUND

Proton Therapy (PT) is a cancer treatment technology that uses high energy protons to penetrate a patient's body and deposit energy into treatment areas such as cancerous tumors. PT systems commonly implement a rotating gantry wheel that directs the proton beam to the patient from any angle between zero and 360 degrees. This allows the physician to design a treatment plan that attacks cancerous tumors from different angles and reduces radiation damage to critical organs and/or healthy tissue.

The charged protons may be generated in a particle accelerator, commonly referred to as a cyclotron and/or a synchrotron, and directed to the patient in the form of a beamline using a series of magnets that guide and shape the particle beamline such that the particles penetrate the patient's body at a selected location and are deposited at the site of the treatment volume. Particle therapy leverages the Bragg Peak property of charged particles such that the majority of the energy is deposited within the last few millimeters of travel along the beamline—at a point commonly referred to as the isocenter, as opposed to conventional, intensity modulated radiation therapy (i.e., photons) in which the majority of energy is deposited in the first few millimeters of travel, thereby undesirably damaging healthy tissue.

Particle therapy treatment facilities typically consist of a single cyclotron and a plurality of treatment rooms. Thus, the single cyclotron is often adapted to generate a particle beamline that is then selectively directed to one of the various treatment rooms. A particle therapy treatment may include the selection of a desired energy level for the beamline, such that the energy of the particles is deposited substantially at the desired location (i.e., the treatment volume) inside the patient's body. Therefore, the energy level selection is directly related to the position and shape of the treatment volume within the patient's body. Frequently, the cyclotron will generate a standard high-energy beamline, which may then be selectively modified as desired for the particular treatment protocol.

The beamline may be directed immediately to the patient without the need for any redirection. However, a more common approach is to redirect the beamline using a series of cooperating bending magnets which route the beamline to a proton nozzle mounted on a gantry. FIG. 1 illustrates an example embodiment prior art particle therapy gantry designed to receive and redirect a particle beamline to a patient. As illustrated, the particle therapy gantry 21 includes at least three bending magnets 11A-C to redirect the particle beamline 15 to the gantry's treatment nozzle 13, and eventually the patient 9 positioned on a treatment bed 17. This allows the beamline 15 to be selectively directed to the patient 9 from any angle and permits a physician to design a treatment plan that minimizes undesirable effects on healthy tissue. Stated differently, gantries are frequently adapted to rotate about a patient, and redirect the beamline to be perpendicular to the gantry's axis of rotation 19, illustrated by the directional arrow 19' in FIG. 1. Thus, the treatment nozzle 13 and beamline 15 may be rotated about the patient 9 such that the beamline 15 is able to penetrate the patient's body at a plurality of locations and encounter the treatment volume from multiple directions. This minimizes adverse effects on healthy tissue and increases the efficacy of the treatment.

Thus, in comparison to standard x-ray therapy, proton therapy is capable of significantly improving dose localization by increasing the dose delivered to the target volume, while minimizing the dose delivered to the surrounding tissue. These improvements are based on the finite penetration range of therapeutic proton beam in the target material. Furthermore, energy deposition to the target material increases as the proton beam slows down and reaches maximum energy near the end of the penetration range. The penetration depth and the location of the energy deposition peak (the Bragg peak) are defined by the proton beam energy. Therefore, a proton beam of a given energy delivers a therapeutic dose of energy at a specific treatment depth. In order to deliver this therapeutic dose to a target with a given extent in depth, proton beams with several different energies can be used.

To provide these several different energies, older proton therapy systems typically changed the proton beam energy in the treatment nozzle by inserting plates of material that attenuate the proton beam energy by the specified amount. More advanced conventional systems change the beam energy further upstream near the proton accelerator itself. Such conventional systems typically require a change of the beam transport line to match each subsequent proton beam energy. Thus, a proton therapy system in which proton beam energies can be changed without such structural changes and adjustments as described above would be desirable.

Another of the challenges facing PT systems is to maintain proper alignment between the proton delivery nozzle and the isocenter of the rotating gantry system when the gantry is rotated to different treatment angles. For example, it is desirable to maintain accuracy of the proton beam to the gantry center when the gantry apparatus is rotated to different positions in order to accurately focus the proton beam to a targeted area of interest. Due to inherent fabrication tolerances and the extreme size and weight of the gantry apparatus and its various components, the structure can deflect when rotated at different angles, allowing the system's center to drift above the target accuracy.

It is known to move the patient bed to compensate for subtle drifts in the system at different angles of rotation. However, moving the patient to compensate for beam misalignment can become quite time consuming and complicated, especially if the treatment plan requires more than one application angle for each patient. Therefore, it is desirable to provide a proton therapy system having a smaller and lighter gantry wheel to avoid some of the structure based deflection.

BRIEF SUMMARY

The present general inventive concept, in various example embodiments, includes a proton therapy system provided with a superconducting beamline. This lighter beamline allows various example embodiments to include a smaller and/or lighter gantry, and/or a reduced deflection of the beamline during rotation of the gantry. A superconducting beamline deflector may be provided with a housing to maintain the position of the various components of the superconducting beamline deflector relative to one another during rotation of the gantry.

Example embodiments of the present general inventive concept may be achieved by providing a proton beam delivery system for a proton treatment system, including a proton beam nozzle to emit a proton beam having a predetermined energy level to a targeted region of a patient, a gantry wheel to support the proton beam nozzle proximate a circumferential surface of the gantry wheel, the gantry wheel being configured to rotate the proton beam nozzle about a rotation axis of the gantry wheel such that the proton beam nozzle emits the proton beam to an isocenter of the gantry wheel corresponding to the targeted region, a beamline deflector configured to be rotated by the gantry wheel to transport the proton beam along a curvilinear path of the beamline deflector from the rotation axis to the proton beam nozzle using a predetermined power setting of the beamline deflector, and a rigid support structure to support the beamline deflector such that when the gantry wheel is rotated to a plurality of positions around the isocenter, the support structure maintains the curvilinear path of the beamline deflector at each position such that the proton beam nozzle directs the proton beam having the predetermined energy level to the isocenter using the same predetermined power setting and energy level at each position.

The beamline deflector may include two or more bending magnets to transport the proton beam along a curved portion of the curvilinear path.

The beamline deflector may include one or more steering magnets to transport the proton beam along a linear portion of the curvilinear path.

The beamline deflector may include a first end section provided with a first bending magnet to bend the proton beam, and the proton delivery system may further include a rear bearing to which the first end section of the beamline deflector is coupled, and through which the proton beam is delivered to the beamline deflector from a proton beam source.

The beamline deflector may further include a second end section coupled to the proton beam nozzle and provided with a second bending magnet to bend the proton beam, the second end section being coupled to the gantry wheel.

The beamline deflector may further include a middle section coupled at both ends respectively to the first and second end sections, and provided with one or more steering magnets to steer the proton beam along a linear portion of the curvilinear path.

The rigid support structure may be configured as a housing to encase at least a majority of surface area of the first, middle, and end sections of the beamline deflector.

The rigid support structure may be configured as a skeletal structure that encloses less than a majority of surface area of the first, middle, and end sections of the beamline deflector to provide ready access to one or more components of the beamline deflector.

The rigid support structure may include a plurality of rigid members that are each coupled to at least one adjacent one of the rigid members to form the rigid support structure.

Two or more components of the beamline deflector may all be respectively coupled to at least one of the rigid members.

The rigid support structure may be provided with one or more additional support members that are extendable to a support surface below the superconducting beamline deflector.

The beamline deflector may be a superconducting beamline deflector.

The beamline deflector may include deflecting members configured such that deflections of the proton beam at entrance and exit points of the deflecting members are less than 1 mm.

Each of the entrance and exit points may define an inflection point having a predetermined slope, and the rigid support structure may support the deflecting members when the gantry wheel is rotated such that the predetermined slope is consistent within a range less than or equal to 0.3 mm/m.

Example embodiments of the present general inventive concept may also be achieved by providing a proton beam delivery system for a proton treatment system, including a proton beam nozzle to emit a proton beam to a targeted region of a patient, and a beamline deflector having a plurality deflecting members, the deflecting members each having a distinct linear slope maintained by a rigid structure to define a curvilinear path to transport a proton beam having a predetermine energy level through the curvilinear path to the proton beam nuzzle using a predetermined power setting of the beamline deflector.

The deflecting members may be configured such that deflections of the proton beam at entrance and exit points of the deflecting members are less than 1 mm.

The rigid structure may include carbon fiber, carbon nanotubes, graphene, composite, any combination thereof, and/or other material having an Elastic Modulus at least three times greater than 30E6 N/m2.

A rear bearing may be provided proximate an end of the beamline deflector that receives the proton beam from the proton generator to support at least a portion of weight of the beamline deflector.

Example embodiments of the present general inventive concept may also be achieved by providing a method of delivering a proton beam in a proton treatment system, the method including rotating a gantry wheel, the gantry wheel being configured to rotate a proton beam nozzle supported proximate a circumferential surface of the gantry wheel about a rotation axis of the gantry wheel such that a proton beam nozzle is positioned to emit a proton beam to an isocenter of the gantry wheel corresponding to a targeted region of a patient, transporting the proton beam by a beamline deflector along a curvilinear path from the rotation axis to the proton beam nozzle using a predetermined power setting of the beamline deflector to direct the proton beam having a predetermined energy level along the curvilinear path, the beamline deflector being supported by a rigid support structure such that when the gantry wheel is rotated to a plurality of positions around the isocenter, the proton beam nozzle directs the proton beam from each position to the isocenter, emitting the proton beam having the predetermined energy level through the beamline deflector using the same predetermined power setting to the targeted region of the patient Additional features and embodiments of the present general inventive concept will be set forth in part in the description which follows, and, in part, will be obvious from the description, or may be learned by practice of the present general inventive concept.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity.

A wide variety of additional embodiments will be more readily understood and appreciated through the following detailed description of the example embodiments, with reference to the accompanying drawings in which:

FIG. 11 illustrates a proton beam delivery system according to an example embodiment of the present general inventive concept

DETAILED DESCRIPTION

Figure 1:
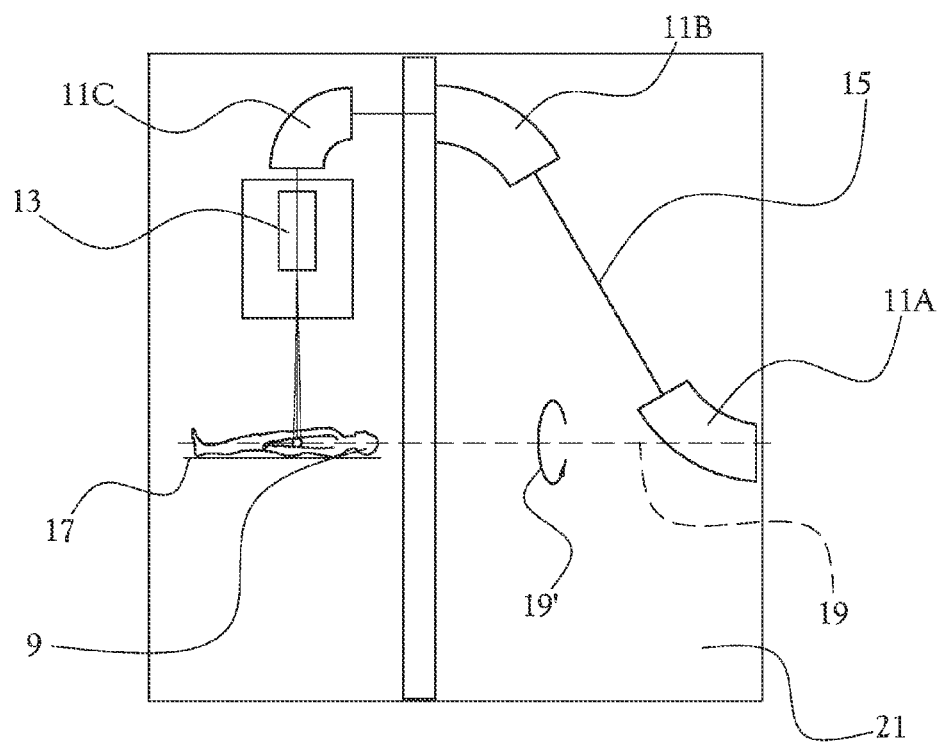
FIG. 1 illustrates an example embodiment of a prior art particle therapy system designed to receive and redirect a particle beamline to a patient.

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

According to various examples of the present general inventive concept, a proton therapy system is provided with a superconducting beamline. This lighter beamline allows various example embodiments to include a smaller and/or lighter gantry, and/or a reduced deflection of the beamline during rotation of the gantry. A superconducting beamline deflector may be provided with a housing to maintain the position of the various components of the superconducting beamline deflector relative to one another during rotation of the gantry. With such a rigid support structure for the superconducting beamline deflector, the beam steering typically associated with gantry rotation in conventional proton therapy systems may be avoided, and thus various such corresponding problems as increased heat, eddy currents, etc., may be eliminated by maintaining the same beamline deflection settings throughout the rotation of the gantry.

One advantage provided by a superconducting beamline is the significant weight reduction of the beamline. Various example embodiments of the present general inventive concept are able to leverage this lower weight by reducing the total deflection of the beamline during the rotation of the gantry to which the beamline is coupled, due to the ability to more easily rotate the lighter components of the superconducting beamline and to the reduced gravitational stress at various points of the system. Typically, in a conventional proton therapy system, steering magnets are utilized to correct deviations in the beam's path as the gantry is rotated to different points around a patient. With the superconducting beamline, a proton therapy system according to various example embodiments of the present general inventive concept may be designed with a rigid gantry that has a single set of beam transport settings that allows for full rotation with beam steering. In other words, due to the rigidity and/or reduced weight of the superconducting beamline, the same beamline settings can be used to deliver the beamline to a given target area at any of the points in the 360 degree rotation of the gantry.

To steer a particle beamline through a gantry system, the beamline is deflected at several entry and exit points of various components and bending magnets. To determine the amounts of deflections and allowable variances in the beamline at different settings and/or positions of the gantry system, calculated deflections may be used inside a beam transport stimulation (such as TURTLE). During testing, it was determined that a gantry according to an embodiment of the present general inventive concept can deflect 16× the provided numbers without affecting the beam's spot size. Such a margin may be increased when testing both the deflection and beam transport in actual constructed embodiments of the present general inventive concept, rather than in simulations.

Figure 2:
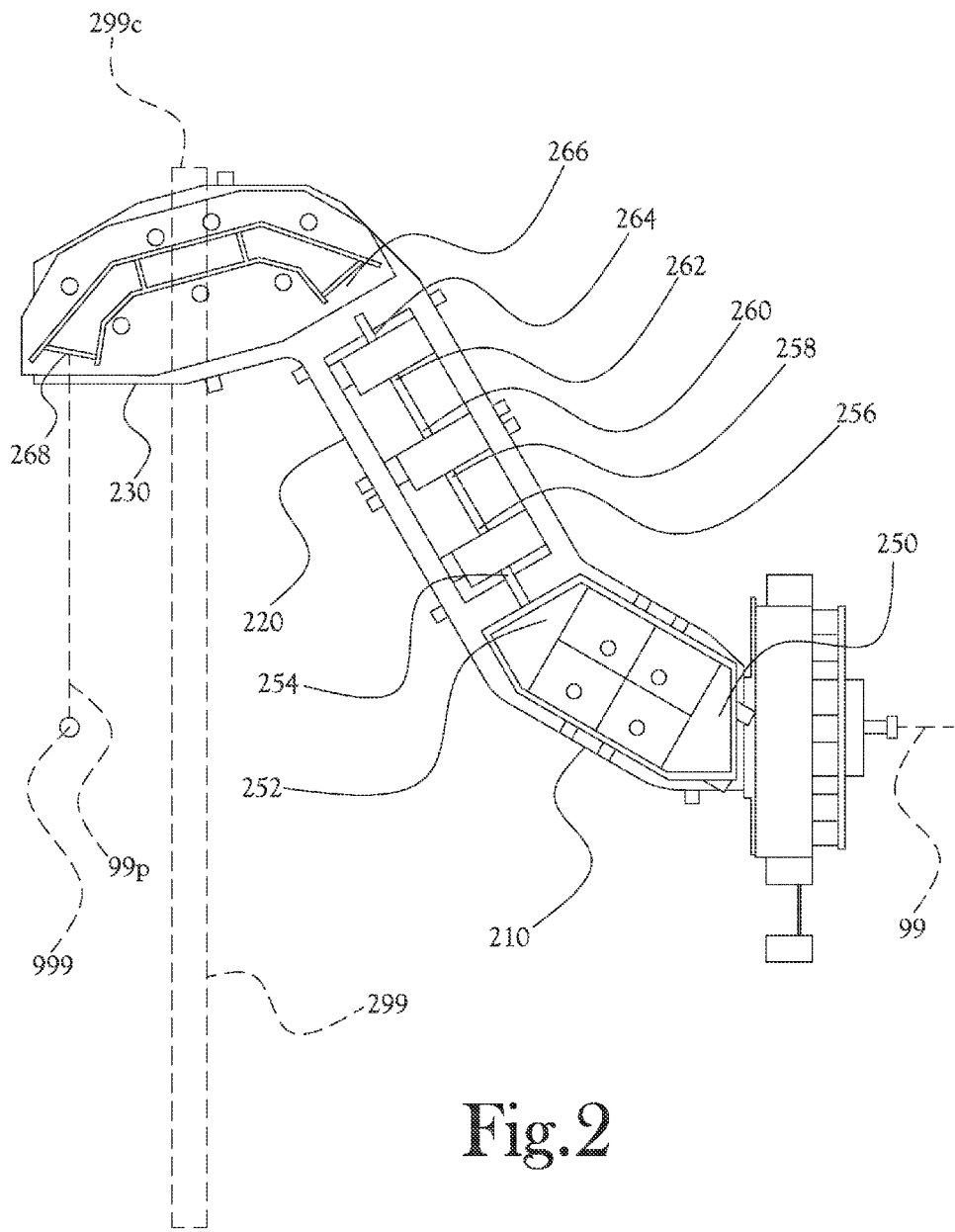
FIG. 2 illustrates a superconducting beamline deflector according to an example embodiment of the present general inventive concept.

FIG. 2 illustrates a proton delivery system including a beamline deflector 200, which may be a superconducting beamline deflector, defining a curvilinear path from the rotation axis 99 to an exit 268 point to transport a proton beam to a proton beam nozzle, according to an example embodiment of the present general inventive concept. A first end section 210 of the superconducting beamline deflector 200 is supported at a rear bearing 215 to define a curved portion of the curvilinear path, and includes a bending magnet to bend an incoming proton beam relative to the line of entry 99 at which the proton beam arrives. A second end section 230 is supported proximate (e.g., adjacent to) a circumferential surface 299c of a gantry wheel 299 (shown in phantom by way of example, but not by way of limitation) extending from a front face of the gantry wheel, the second end section 230 including one or more bending magnets to bend the proton beam to a radial line 99p substantially perpendicular to the axis of rotation 99 of the superconducting beamline deflector 200 so that the proton beam is beamed toward an isocenter 999 of the gantry wheel corresponding to a targeted region of a patient. A middle section 220 steers the beamline between the first end section 210 and the second end section 230 along a linear portion of the curvilinear path.

In the example embodiment illustrated in FIG. 2, the middle section 220 includes three steering magnets 222, 224, 226. However, it is noted that various example embodiments of the present general inventive concept may include more or fewer bending and/or steering magnets than those illustrated in FIG. 2, along with various different orientations and/or connections. The first end section 210, middle section 220, and second end section 230 share a common housing 205 that provides a rigid support for the components supported therein such that the shape of the superconducting beamline deflector 200 and curvilinear path is maintained at all points of a 360 degree rotation of the gantry wheel. For ease of understanding, the housing 205 of FIG. 2 is illustrated as a continuous casing that surrounds all of the components of the first end section 210, middle section 220, and second end section 230, but it is understood that various example embodiments of the present general inventive concept may provide any of a number of housing configurations. For example, various example embodiments may include a housing 205 with two or more sections coupled together by known various coupling methods, may have a substantially continuous surface, may have a skeletal surface to provide ready access to components housed therein, and so on. A common characteristic of the various example embodiments of the housing 205 is a rigid structure to maintain the shape of the superconducting beamline deflector 200 during gantry rotation. The rigidity is facilitated from the design of the load paths which carry the weight from the beamline deflector 200. Additionally, rigidity comes from the Young's Modulus of the material selected. Today steel has been applied due to its combination of cost, machinability, strength, and Young's Modulus however carbon fiber, carbon nanotubes, and graphene all are options to provide more rigidity because the Young's Modulus is 3 to 4 times higher than steel.

During development of the gantry including the superconducting beamline deflector 200, it was noted that supporting the beamline at the rear bearing 215 and at the front wall may cause a "saddle" in the beamline deflector 200. During a determination of the slope of deflection that may be implemented, an example theoretical gantry beamline slope was suggested to be 0.1 mm per meter. The gantry trusses between the rear 215 bearing and the gantry wheel were then deflection optimized to achieve that target value.

During gantry fabrication, these design numbers were provided to testers to evaluate whether the deflection results met the testing requirements. It was determined that there was a deflection factor of safety beyond 16. Therefore, it was determined that the gantry according to this example embodiment of the present general inventive concept should be sufficient to hold the rotating beamline stiff enough to allow for a single beam transport setting throughout the 360 degree rotation. In other words, the stiffness of the housing 205 provides a structural support stable enough to rotate the gantry to any point in 360 degrees of possible rotation without having to adjust the power provided to the bending and/or steering magnets while using the same proton beam energy.

FIGS. 3-6 illustrate testing results of deflection values in an example embodiment of the present general inventive concept at four different rotation positions of the gantry system. During FEA simulations of this example embodiment of the present general inventive concept, the simulations each use gravity as the only loading condition on the superconducting beamline deflector of the gantry system. The gantry loading was simulated at 0 degrees (12 o'clock), illustrated in FIG. 3, −45 degrees (10:30), illustrated in FIG. 4, −90 degrees (9 o'clock), illustrated in FIG. 5, and −180 degrees (6 o'clock), illustrated in FIG. 6. Each model dimension controlled the isocenter to have a negligible offset.

Deflection was probed at the entrance and exit of each magnet illustrated in FIG. 2. As illustrated in FIG. 2, the probe points include the entrance 250 and exit 252 of the bending magnet provided in the first end section 210, the respective entrances 254,258,262 and exits 256,260,264 of the steering magnets 222,224,226 provided in the middle section 220, and the entrance 266 and exit 268 of the bending magnet provided in the second end section 230. The objective of the simulation was to analyze FEA simulation results for beamline deflection, and the intended outcome was to demonstrate sub millimeter deflection. Assumptions in the simulation included a 36 ksi yield and standard A36 SW material properties for low stress regions, and higher grades 60-80 ksi yield through major structural members. The simulations included Solidworks Simulations and Alpha Gantry models.

Figure 3:
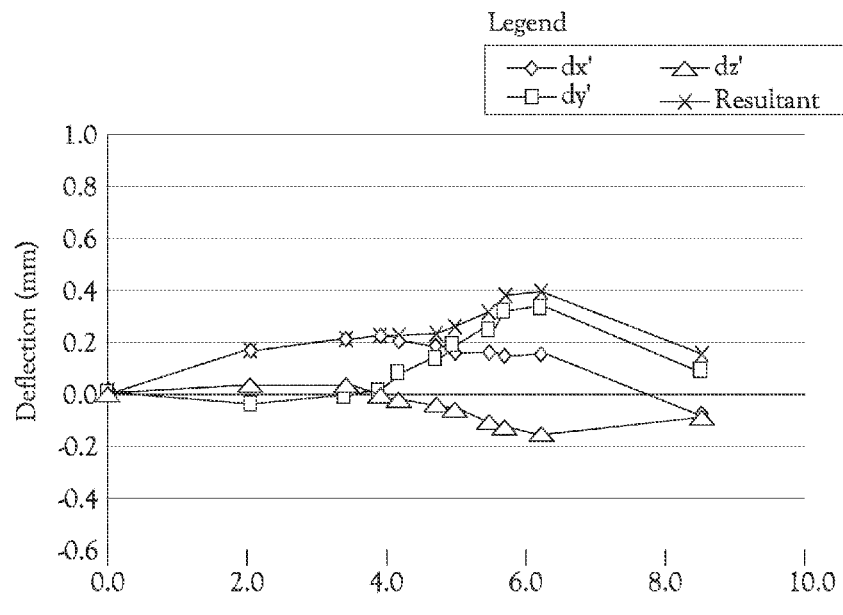
FIGS. 3-6 illustrate testing results of deflection values in an example embodiment of the present general inventive concept at four different rotation positions of the gantry system.
Figure 4:
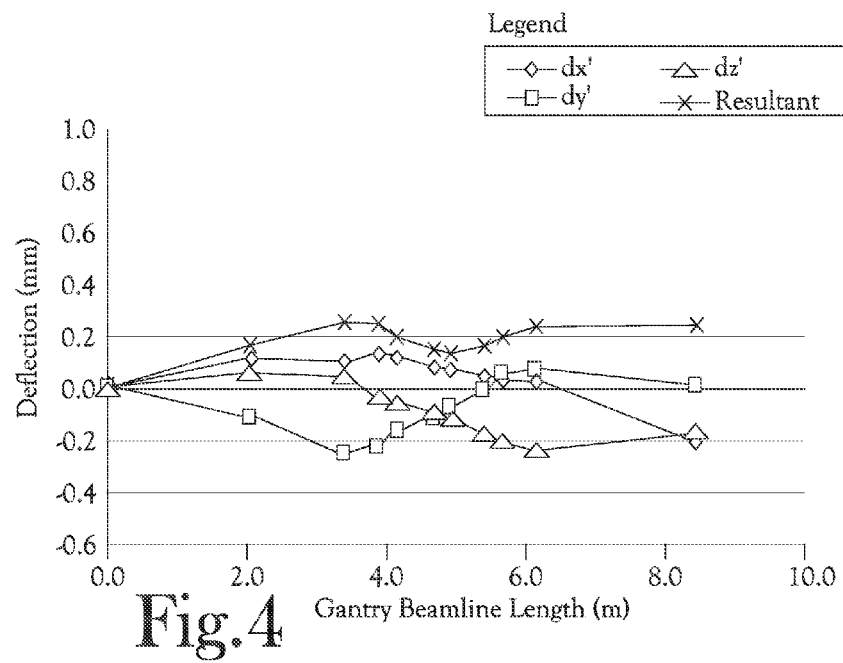
Figure 5:
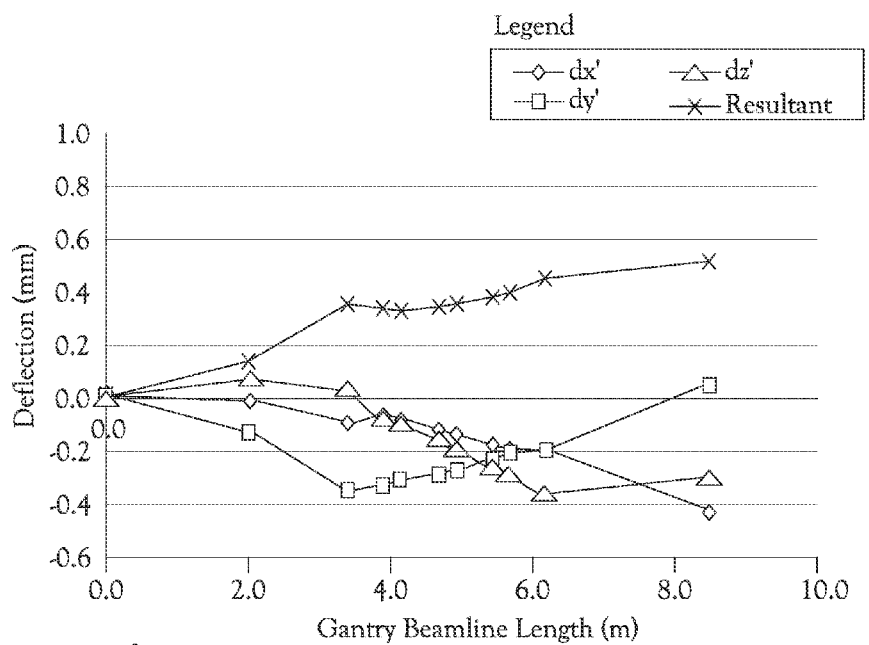
Figure 6:
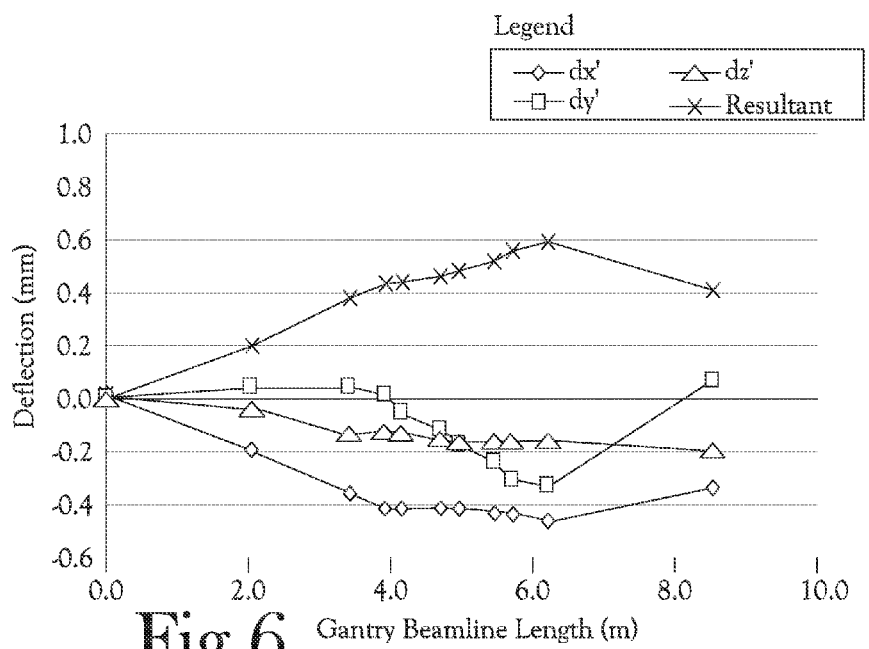

FIG. 3 illustrates the beamline deflections encountered when the gantry is positioned such that the superconducting beamline deflector 200 is positioned at 0 degrees, showing the dx', dy', dz', and the resultant deflection values at each of the ten magnet entrances and exits illustrated in FIG. 2. It is shown in FIG. 3 that at the 0 degrees position, gantry deflection is well less than 1 mm throughout all of the evaluated magnet entrance and exit points. The maximum resulting gantry deflection of approximately 0.4 mm appears at the entrance 266 of the bending magnet provided in the second end section 230, which is the entrance point of the last magnet in the beamline, or superconducting beamline deflector 200. The gantry deflection values encountered while the superconducting beamline deflector 200 is positioned at −45, −90, and 180 degrees are similarly illustrated in FIGS. 4-6, respectively.

Figure 7:
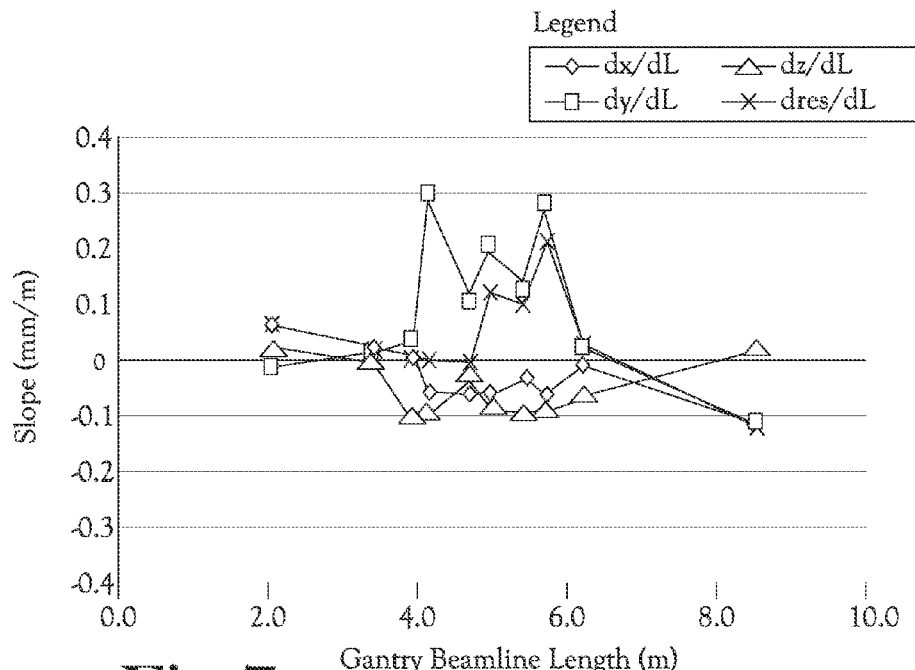
FIGS. 7-10 illustrate testing results of gantry slope values in an example embodiment of the present general inventive concept at four different rotation positions of the gantry system.
Figure 8:
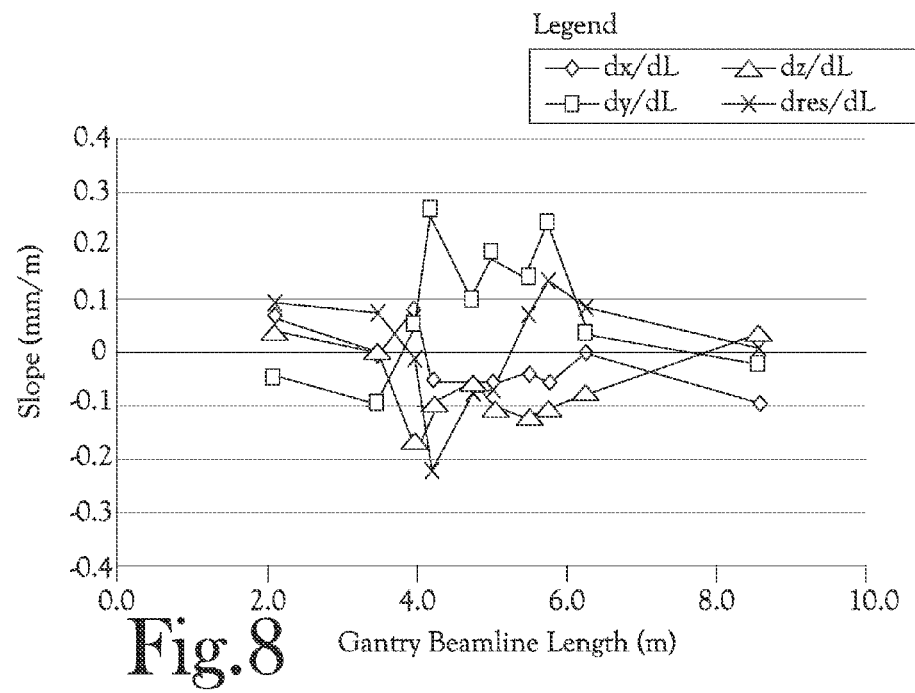
Figure 9:
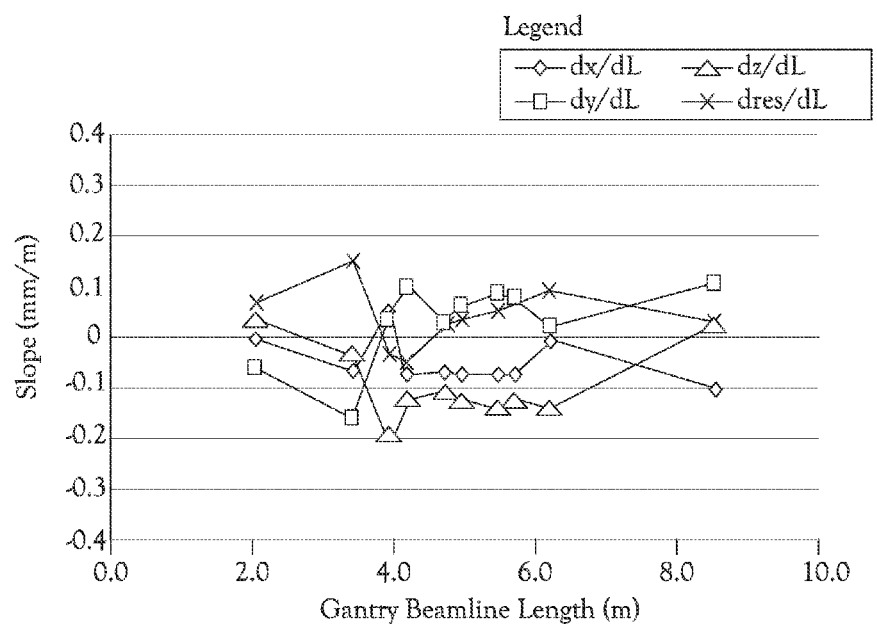
Figure 10:
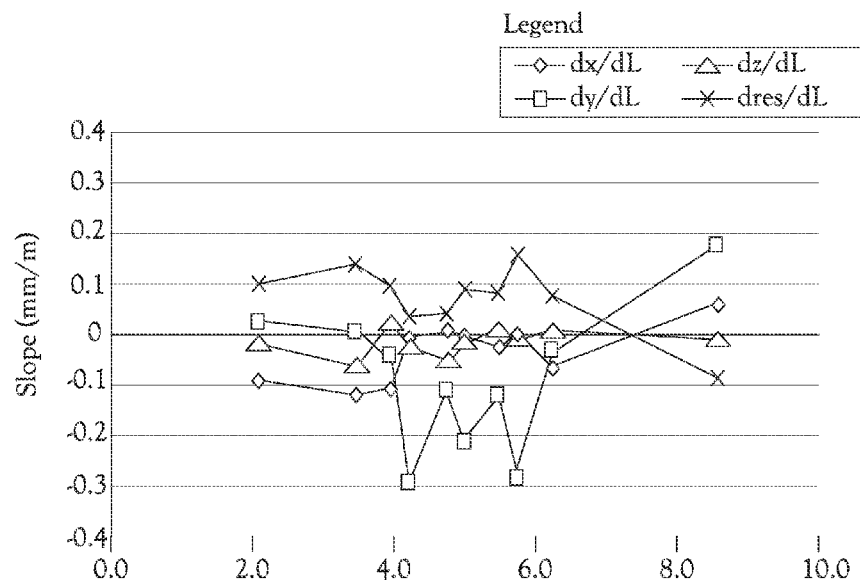

FIGS. 7-10 illustrate testing results of gantry slope values in an example embodiment of the present general inventive concept at four different rotation positions of the gantry system. FIG. 7 illustrates the gantry slope when the gantry is positioned such that the superconducting beamline deflector 200 is positioned at 0 degrees, showing the dx/dL, dy/dL, dz/dL, and dres/dL values at each of the ten magnet entrances and exits illustrated in FIG. 2. As shown in FIG. 7, the maximum resulting slope, in millimeters per meter, is 0.3 at the exit point 256 of the first steering magnet 222 of the middle section 220 of the superconducting beamline deflector 200. The gantry slope values encountered while the superconducting beamline deflector 200 is positioned at −45, −90, and 180 degrees are similarly illustrated in FIGS. 8-10, respectively. This consistent value of the slope within a range less than or equal to 0.3 mm/m would not be expected in a typical gantry system where very large and heavy components are rotated causing large stresses and sagging of the components and changes in slope of the inflection points of the curvilinear path greater than 0.3 mm/m.

It was concluded from these simulations that the gantry deflection is comprised of three distinct linear slopes; from the rear bearing to the middle, the middle to the wheel, and the wheel to the isocenter. All deflection values at the entrance and exit points of the bending and steering magnets were less than 1 mm, and the slopes were consistent between the inflection points. The results indicate that if onboard, these inflection points may be optimal for beam steering. Also, it was determined that the gantry's deflection can be further reduced with additional support provided between one or more portions of the superconducting beamline detector and the supporting surface.

FIG. 11 illustrates a proton beam delivery system for use in a proton therapy system according to an example embodiment of the present general inventive concept. As illustrated in FIG. 11, the proton delivery system 400 includes one or more bending magnets 420a, 420b, or achromatic bends, and a middle section 450, to redirect a proton beam 490 from a proton source 480 through a curvilinear path to a target area 430 of a patient using a predetermined power setting for the proton delivery system 400. The middle section 450 defines a linear portion of the curvilinear path, and the bending magnets 420a, 420b define a curved portion of the curvilinear path. The middle section 450 can include one or more steering magnets to direct the proton beam through the linear portion. A rigid housing 410 is provided to support the bending magnets 420a, 420b and middle section 450 so that the same structural position of the housed components is maintained as the gantry of the proton beam delivery system is rotated through a 360 degrees or less rotation. The bending magnets 420a, 420b and the one or more steering magnets of the middle section 450 are connected to a power source 440 to provide power settings to the bending magnets 420a, 420b and the one or more steering magnets. A controller 460, also referred to as a power changing unit, can be provided to change the power settings applied to the bending and steering magnets. The power changing unit 460 can also be connected to the proton source 480 to change the energy level of the proton beam 490 generated by the proton source 480. Although not illustrated in FIG. 11, additional support may be provided between a support surface and proton delivery system to aid in maintaining the structural position of the components relative to one another during gantry rotation. For example, an extendable member may be provided to offer additional support between the support surface and the superconducting beamline deflector. According to various example embodiments, the extendable member may be coupled at one end to the superconducting beamline deflector and extend to the support surface in a variety of different configurations such as, for example, a telescoping support member, a pivoting member, a sliding member, and so on. According to various example embodiments of the present general inventive concept, two or more such support members may be provided to the superconducting beamline deflector.

Various example embodiments of the present general inventive concept provide a superconducting beamline deflector and a gantry having a single set of beam transport settings that allows for full rotation with beam steering. The superconducting beamline deflector may be provided with a housing to maintain the position of the various components of the superconducting beamline deflector relative to one another during rotation of the gantry.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein, using sound engineering judgment. Numerous variations, modification, and additional embodiments are possible, and, accordingly, all such variations, modifications, and embodiments are to be regarded as being within the spirit and scope of the present general inventive concept.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

The invention claimed is:

1. A proton beam delivery system for a proton treatment system, comprising:
   a proton beam nozzle to emit a proton beam having a predetermined energy level to a targeted region of a patient;
   a gantry wheel to support the proton beam nozzle proximate a circumferential surface of the gantry wheel, the gantry wheel being configured to rotate the proton beam nozzle about a rotation axis of the gantry wheel such that the proton beam nozzle emits the proton beam to an isocenter of the gantry wheel corresponding to the targeted region;
   a beamline deflector configured to be rotated by the gantry wheel to transport the proton beam along a curvilinear path of the beamline deflector from the rotation axis to the proton beam nozzle using a predetermined power setting of the beamline deflector; and
   a common housing rigid support structure to support the beamline deflector such that when the gantry wheel is rotated to a plurality of positions around the isocenter, the common housing rigid support structure maintains the curvilinear path of the beamline deflector at each position such that the proton beam nozzle directs the proton beam having the predetermined energy level to the isocenter using the same predetermined power setting and energy level at each position.

2. The proton beam delivery system of claim 1, wherein the beamline deflector comprises two or more bending magnets to transport the proton beam along a curved portion of the curvilinear path.

3. The proton beam delivery system of claim 2, wherein the beamline deflector comprises one or more steering magnets to transport the proton beam along a linear portion of the curvilinear path.

4. The proton beam delivery system of claim 1, wherein the beamline deflector comprises a first end section provided with a first bending magnet to bend the proton beam; and
   further comprising a rear bearing to which the first end section of the beamline deflector is coupled, and through which the proton beam is delivered to the beamline deflector from a proton beam source.

5. The proton beam delivery system of claim 4, wherein the beamline deflector further comprises a second end section coupled to the proton beam nozzle and provided with a second bending magnet to bend the proton beam, the second end section being coupled to the gantry wheel.

6. The proton beam delivery system of claim 5, wherein the beamline deflector further comprises a middle section coupled at both ends respectively to the first and second end sections, the middle section including one or more steering magnets to steer the proton beam along a linear portion of the curvilinear path.

7. The proton beam delivery system of claim 6, wherein the common housing rigid support structure is configured as a housing to encase at least a majority of surface area of the first, middle, and end sections of the beamline deflector.

8. The proton beam delivery system of claim 6, wherein the common housing rigid support structure is configured as a skeletal structure that encloses less than a majority of surface area of the first, middle, and end sections of the beamline deflector to provide ready access to one or more components of the beamline deflector.

9. The proton beam delivery system of claim 1, wherein the common housing rigid support structure comprises a plurality of rigid members that are each coupled to at least one adjacent one of the rigid members to form the common housing rigid support structure.

10. The proton beam delivery system of claim 9, wherein two or more components of the beamline deflector are all respectively coupled to at least one of the rigid members.

11. The proton beam delivery system of claim 9, wherein the common housing rigid support structure is provided with one or more additional support members that are extendable to a support surface below the beamline deflector.

12. The proton beam delivery system of claim 1, wherein the beamline deflector is a superconducting beamline deflector.

13. The proton beam delivery system of claim 1, wherein the beamline deflector includes deflecting members configured such that deflections of the proton beam at entrance and exit points of the deflecting members are less than 1 mm.

14. The proton beam delivery system of claim 13, wherein each of the entrance and exit points defines an inflection point having a predetermined slope, and the common housing rigid support structure supports the deflecting members when the gantry wheel is rotated such that the predetermined slope is consistent within a range less than or equal to 0.3 mm/m.

15. A proton beam delivery system for a proton treatment system, comprising:
a proton beam nozzle to emit a proton beam to a targeted region of a patient;
a beamline deflector having a plurality of deflecting members to deflect the proton beam along a curvilinear path of the beamline deflector, the deflecting members each having a distinct linear slope to transport a proton beam having a predetermined energy level through the curvilinear path from a proton beam generator to the proton beam nozzle using a predetermined power setting of the beamline deflector; and
a common housing rigid structure connected to the beamline deflector to maintain the distinct linear slopes of the curvilinear path.

16. The proton beam delivery system of claim 15, wherein the deflecting members are configured such that deflections of the proton beam at entrance and exit points of the deflecting members are less than 1 mm.

17. The proton beam delivery system of claim 15, wherein the common housing rigid structure is comprised of carbon fiber, carbon nanotubes, graphene, composite, any combination thereof, and/or other material having an Elastic Modulus at least three times greater than 30E6 N/m2.

18. The proton beam delivery system of claim 15, wherein a rear bearing is provided proximate an end of the beamline deflector that receives the proton beam from the proton generator to support at least a portion of weight of the beamline deflector.

19. A method of delivering a proton beam in a proton treatment system, the method comprising:
rotating a gantry wheel, the gantry wheel being configured to rotate a proton beam nozzle supported proximate a circumferential surface of the gantry wheel about a rotation axis of the gantry wheel such that a proton beam nozzle is positioned to emit a proton beam to an isocenter of the gantry wheel corresponding to a targeted region of a patient;
transporting the proton beam by a beamline deflector along a curvilinear path from the rotation axis to the proton beam nozzle using a predetermined power setting of the beamline deflector to direct the proton beam having a predetermined energy level along the curvilinear path, the beamline deflector being supported by a common housing rigid support structure such that when the gantry wheel is rotated to a plurality of positions around the isocenter, the proton beam nozzle directs the proton beam from each position to the isocenter; and
emitting the proton beam having the predetermined energy level through the beamline deflector using the same predetermined power setting to the targeted region of the patient.

20. The method of claim 19 wherein the beamline deflector is a superconducting beamline deflector.

* * * * *